US00PP34760P2

(12) United States Plant Patent
Beers

(10) Patent No.: US PP34,760 P2
(45) Date of Patent: Nov. 22, 2022

(54) ***GERBERA* PLANT NAMED 'MAJLIP20AA'**

(50) Latin Name: *Gerbera hybrida*
Varietal Denomination: MAJLIP20AA

(71) Applicant: HilverdaFlorist B.V., De Kwakel (NL)

(72) Inventor: Martin Beers, Hoofddorp (NL)

(73) Assignee: HilverdaFlorist B.V., De Kwakel (NL)

( * ) Notice: Subject to any disclaimer, the term of this patent is extended or adjusted under 35 U.S.C. 154(b) by 0 days.

(21) Appl. No.: 17/747,743

(22) Filed: May 18, 2022

Related U.S. Application Data

(60) Provisional application No. 63/192,017, filed on May 22, 2021.

(51) Int. Cl.
*A01H 5/02* (2018.01)
*A01H 6/14* (2018.01)

(52) U.S. Cl.
USPC ..... Plt./357

(58) Field of Classification Search
USPC ..... Plt./357
See application file for complete search history.

*Primary Examiner* — Susan McCormick Ewoldt
(74) *Attorney, Agent, or Firm* — C. Anne Whealy

(57) ABSTRACT

A new and distinct cultivar of *Gerbera* plant named 'MAJLIP20AA', characterized by its broadly upright and uniformly mounding plant habit; moderately vigorous to vigorous growth habit; dense and bushy appearance; numerous inflorescences with deep pink-colored ray florets; upright and moderately strong peduncles; good garden performance and relative tolerance to low temperatures.

1 Drawing Sheet

Botanical designation: *Gerbera hybrida.*
Cultivar denomination: 'MAJLIP20AA'.

BACKGROUND OF THE INVENTION

The present invention relates to a new and distinct cultivar of *Gerbera* plant, botanically known as *Gerbera hybrida* and hereinafter referred to by the cultivar name 'MAJLIP20AA'.

The new *Gerbera* plant is a product of a planned breeding program conducted by the Inventor in De Kwakel, The Netherlands. The objective of the breeding program is to create new garden *Gerbera* plants with numerous attractive inflorescences, resistant to cold temperatures and good garden performance.

The new *Gerbera* plant originated from a cross-pollination in March, 2014 of a proprietary selection of *Gerbera hybrida* identified as code number 10T0518, not patented, as the female, or seed, parent with a proprietary selection of *Gerbera hybrida* identified as code number 13T1031, not patented, as the male, or pollen, parent. The new *Gerbera* plant was discovered and selected as a single flowering plant from within the progeny of the stated cross-pollination in a controlled greenhouse environment in De Kwakel, The Netherlands in June, 2015.

Asexual reproduction of the new *Gerbera* plant by vegetative terminal cuttings and in vitro meristem culture in De Kwakel, The Netherlands, since August, 2015 has shown that the unique features of this new *Gerbera* plant are stable and reproduced true to type in successive generations of asexual reproduction.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MAJLIP20AA'. These characteristics in combination distinguish 'MAJLIP20AA' as a new and distinct *Gerbera* plant:

1. Broadly upright and uniformly mounding plant habit.
2. Moderately vigorous to vigorous growth habit.
3. Dense and bushy appearance.
4. Numerous inflorescences with deep pink-colored ray florets.
5. Upright and moderately strong peduncles.
6. Good garden performance and relative tolerance to low temperatures.

Plants of the new *Gerbera* differ primarily from plants of the female parent selection in the following characteristics:

1. Plants of the new *Gerbera* have larger inflorescences with larger ray florets than plants of the female parent selection.
2. Plants of the new *Gerbera* have deep pink-colored ray florets whereas plants of the female parent selection have light orange-colored ray florets.

Plants of the new *Gerbera* differ primarily from plants of the male parent selection in ray floret color as plants of the new *Gerbera* have lighter pink-colored ray florets than plants of the male parent selection.

Plants of the new *Gerbera* can be compared to plants of the *Gerbera hybrida* 'GLOLIP21AA', disclosed in a U.S. Plant patent application Ser. No. 17/747,718 filed concurrently. In side-by-side comparisons, plants of the new *Gerbera* differ from plants of 'GLOLIP21AA' in the following characteristics:

1. Plants of the new *Gerbera* are more vigorous than plants of 'GLOLIP21AA'.

2. Plants of the new *Gerbera* have smaller leaves than plants of 'GLOLIP21AA'.
3. Plants of the new *Gerbera* have smaller inflorescences than plants of 'GLOLIP21AA'.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant.

The photograph is a side perspective view of a typical flowering plant of 'MAJLIP20AA' grown in a container.

DETAILED BOTANICAL DESCRIPTION

The aforementioned photograph and following observations and measurements describe plants grown during the winter and early spring in 17-cm containers in a glass-covered greenhouse in De Kwakel, The Netherlands and under cultural practices typical of commercial garden *Gerbera* production. During the production of the plants, day and night temperatures ranged from 12° C. to 16° C. Plants were six months old when the photograph was taken and 20 weeks old when the description was taken. In the following description, color references are made to The Royal Horticultural Society Colour Chart, 2015 Edition, except where general terms of ordinary dictionary significance are used.

Botanical classification: *Gerbera hybrida* 'MAJLIP20AA'.

Parentage:

*Female, or seed, parent*.—Proprietary selection of *Gerbera hybrida* identified as code number 10T0518, not patented.

*Male, or pollen, parent*.—Proprietary selection of *Gerbera hybrida* identified as code number 13T1031, not patented.

Propagation:

*Type*.—By cuttings and in vitro meristem culture.

*Time to initiate roots, by cuttings, summer and winter*.—About 3.5 weeks at minimum temperatures of 20° C.

*Time to initiate roots, by tissue culture, summer and winter*.—About 2.5 to 3 weeks at minimum temperatures of 20° C.

*Time to produce a rooted young plant, by cuttings, summer and winter*.—About 3.5 weeks after rooting, at temperatures about 20° C. to 26° C.

*Time to produce a rooted young plant, by tissue culture, summer and winter*.—About five to six weeks at temperatures about 20° C. to 26° C.

*Root description*.—Fibrous; typically white in color, actual color of the roots is dependent on substrate composition, water quality, fertilizer type and formulation, substrate temperature and physiological age of roots.

Plant description:

*Appearance*.—Herbaceous perennial that is typically grown as a container or garden plant; broadly upright and uniformly mounding; roughly flattened globular in shape; numerous leaves arranged in basal rosettes; dense and bushy habit; inflorescences held above the foliar plane on erect and strong basal peduncles; moderately vigorous to vigorous growth habit and moderate growth rate.

*Plant height, soil level to top of foliar plane*.—About 27 cm.

*Plant height, soil level to top of inflorescences*.—About 46.5 cm.

*Plant width or spread*.—About 57 cm

Leaf description:

*Arrangement*.—Alternate, basal, simple.

*Length*.—About 20.6 cm.

*Width*.—About 9 cm.

*Shape*.—Narrowly ovate to narrowly oblong.

*Apex*.—Obtuse.

*Base*.—Broadly attenuate.

*Margin*.—Coarsely repand to coarsely angulate; proximally, coarsely and irregularly angulate to runcinate; sinuses medium to deep and parallel to divergent.

*Texture and luster, upper surface*.—Moderately pubescent; moderately glossy.

*Texture and luster, lower surface*.—Densely pubescent, slightly rugose; matte.

*Venation pattern*.—Pinnate.

*Color*.—Developing leaves, upper surface: Close to a blend of 141A and 143A. Developing leaves, lower surface: Close to 138C. Fully expanded leaves, upper surface: Close to NN137B; venation, close to 144A. Fully expanded leaves, lower surface: Close to a blend of 147C and 148B; venation, close to 146C.

*Petioles*.—Length: About 10.4 cm. Diameter: About 3 mm. Texture and luster, upper and lower surfaces: Moderately to densely pubescent; slightly glossy. Strength: Moderately strong to strong. Color, upper surface: Close to 144A. Color, lower surface: Close to 144A to 144B.

Inflorescence description:

*Appearance*.—Composite inflorescence form with oblanceolate-shaped ray florets; solitary inflorescences borne on upright and moderately strong peduncles and held above the foliar plane; ray and disc florets arranged acropetally on a capitulum; inflorescences face upright.

*Fragrance*.—None detected.

*Flowering season*.—Plants begin flowering about three months after planting; under garden conditions in The Netherlands, plants flower from spring to late autumn; plants can be flowered year-round in the greenhouse.

*Inflorescence longevity*.—Depending on the temperature, inflorescences last about two to four weeks on the plant; inflorescences persistent.

*Quantity of inflorescences*.—Freely flowering habit with about 30 inflorescences developing per plant during the flowering season.

*Inflorescence buds*.—Height: About 2.3 cm. Diameter: About 2.3 cm. Shape: Globular. Texture and luster: Moderately to densely pubescent; matte. Color: Close to 143B and distally, close to 144B; immature ray florets, close to 150C.

*Inflorescence size*.—Diameter: About 7.6 cm. Depth (height): About 3.3 cm. Diameter of disc: About 2.1 cm.

*Receptacles*.—Height: About 3 mm. Diameter: About 3 mm. Shape: Club-shaped. Color: Close to 157D.

*Ray florets*.—Quantity and arrangement: About 120 per inflorescence; ray florets arranged in about four outer whorls and two inner whorls of smaller ray florets. Orientation: Proximally, about 40° from vertical; distally, close to horizontal to slightly downward. Outer whorls of ray florets: Length: About 4.1 cm. Width: About 8.25 mm. Shape: Oblanceolate. Apex: Narrowly obtuse to shallowly emarginate. Base: Narrowly cuneate. Margin: Entire; not undulate. Texture and luster, upper surface: Smooth, glabrous; velvety; matte. Texture and luster, lower surface: Smooth, glabrous; slightly velvety; slightly glossy. Color: When opening, upper surface: Close to 41D. When opening, lower surface: Close to N144D. Fully opened, upper surface: Close to 52C; towards the apex, close to 52D; venation, similar to lamina colors; color does not change with subsequent development. Fully opened, lower surface: Close to a blend of 150C and 151D; towards the base, tinged with close to 49B; venation, similar to lamina colors; color does not change with subsequent development. Inner whorls of ray florets: Length: About 3.1 cm. Width: About 3.25 mm. Shape: Narrowly oblanceolate to narrowly oblong. Apex: Narrowly obtuse to shallowly emarginate. Base: Narrowly cuneate. Margin: Entire; not undulate. Texture and luster, upper surface: Smooth, glabrous; velvety; matte. Texture and luster, lower surface: Smooth, glabrous; slightly velvety; slightly glossy. Color: When opening, upper surface: Close to 39C to 39D. When opening, lower surface: Close to a blend of 150C and 151D. Fully opened, upper surface: Close to 52D; venation, similar to lamina colors; color does not change with subsequent development. Fully opened, lower surface: Close to a blend of 150C and 151D; towards the base, tinged with close to 49B; venation, similar to lamina colors; color does not change with subsequent development.

*Disc florets*.—Quantity and arrangement: About 180 disc florets at center of the inflorescence arranged in about a six-whorl spiral. Length: About 1.7 cm. Width: About 7 mm. Shape: Tubular with one or two narrow free lobes and one broader free lobe. Apex: Acute and recurved; upper 33.3%, free. Base: Lower 66.7%, fused. Margin, free lobes: Entire; not undulate. Texture, upper surface: Smooth, glabrous; moderately velvety; matte. Texture, lower surface: Smooth, glabrous; slightly velvety; slightly glossy. Color: When opening, inner and outer surfaces: Apex, close to a blend of 157C and 158C; mid-section and base, close to 157B. Fully opened, inner surface: Apex, close to 52D; mid-section and base, close to 157A; color does not change with subsequent development. Fully opened, outer surface: Apex, close to 158B tinged with close to 51D; mid-section and base, close to 157A; color does not change with subsequent development.

*Pappus*.—Quantity of hairs per floret: Numerous. Length: About 7 mm. Diameter: Less than 1 mm. Texture and luster: Soft; matte. Color: Close to 182D; towards the base, close to 145D.

*Phyllaries*.—Quantity and arrangement: About 60 per inflorescence arranged in about three whorls. Length: About 1.3 cm. Width (at base): About 2 mm. Shape: Linear. Apex: Narrowly acute. Base: Cuneate. Margin: Entire. Texture and luster, upper surface: Smooth, glabrous; moderately glossy. Texture and luster, lower surface: Moderately to densely pubescent; matte. Color, upper surface: Close to 144A; midvein, close to 143A. Color, lower surface: Close to 144A; towards the base, close to 137B.

*Peduncles*.—Length: About 39.7 cm. Diameter: Proximally, about 5 mm; distally, about 3 mm. Strength: Moderately strong. Angle: About 17.5° from vertical. Texture and luster: Moderately to densely pubescent; moderately glossy. Color: Close to 144A; distally, close to 147B.

*Reproductive organs*.—Androecium (present on disc florets only): Quantity per floret: Five. Filament length: About 5 mm. Filament color: Close to 157D. Anther shape: Linear; basifixed. Anther size: About 4 mm by 0.3 mm. Anther color: Close to 13B. Pollen amount: Scarce. Pollen color: Close to 13C. Gynoecium (present on ray and disc florets): Quantity per floret: One. Pistil length: About 1.2 cm. Stigma diameter: About 0.3 mm. Stigma shape: Cleft. Stigma color: Close to 155A. Style length: About 1.2 cm. Style color: Close to NN155A; distally, tinged with close to 55D. Ovary color: Close to 157A.

*Seeds and fruits*.—To date, seed and fruit production has not been observed on plants of the new *Gerbera*.

Pathogen & pest resistance: To date, resistance to pathogens and pests common to *Gerbera* plants has not been observed on plants of the new *Gerbera* grown under commercial production conditions.

Garden performance: Plants of the new *Gerbera* have been observed to have good garden performance and to tolerate temperatures ranging from about −5° C. to about 35° C. and to be cold hardy to USDA Hardiness Zone 7.

It is claimed:

1. A new and distinct *Gerbera* plant named 'MAJLIP20AA' as illustrated and described.

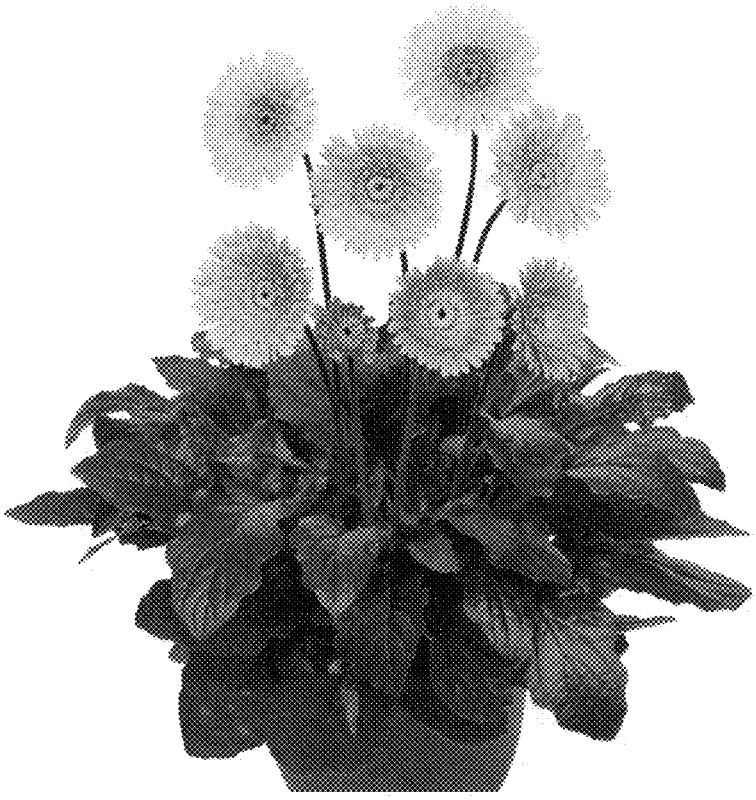

* * * * *